United States Patent [19]

Carter

[11] Patent Number: 4,950,652

[45] Date of Patent: * Aug. 21, 1990

[54] DSRNAS FOR COMBINATION THERAPY IN THE TREATMENT OF VIRAL DISEASES

[75] Inventor: William A. Carter, Birchrunville, Pa.

[73] Assignee: HEM Research, Inc., Rockville, Md.

[*] Notice: The portion of the term of this patent subsequent to Jan. 3, 2006 has been disclaimed.

[21] Appl. No.: 125,097

[22] Filed: Nov. 25, 1987

Related U.S. Application Data

[63] Continuation-in-part of Ser. No. 28,823, Mar. 23, 1987, abandoned.

[51] Int. Cl.$^5$ ............................................. A61K 31/70
[52] U.S. Cl. ........................................ 514/44; 514/50; 514/120; 514/934
[58] Field of Search .................... 514/44, 120, 934; 424/85.1, 85.4, 85.5, 85.6, 85.7

[56] References Cited

U.S. PATENT DOCUMENTS

| | | | |
|---|---|---|---|
| 4,724,232 | 2/1988 | Rideout et al. | 514/50 |
| 4,795,744 | 1/1989 | Carter | 514/44 |

FOREIGN PATENT DOCUMENTS

| | | |
|---|---|---|
| 0113162 | 7/1984 | European Pat. Off. . |
| 0213921 | 3/1987 | European Pat. Off. . |

OTHER PUBLICATIONS

Proc. Ntl. Acad. Sci. U.S.A., Mitsuya et al., vol. 82, pp. 7096-7100, Oct. 1985, "3'-Azido-3'deoxythymidine (BW A509U): An Antiviral Agent that Inhibits . . . ".

Proc. Natl. Acad. Sci. U.S.A., Mitsuya et al., vol. 83, pp. 1914-1915, Mar. 1986, "Inhibition of the in Vitro Infectivity and Cytopathic Effect of Human . . . ".

J. of Biological Response Modifiers, Hubbel et al., 6:525-536, 1987, "Augmented Antitumor Effect of Combined Human Natural Interferon-Alpha . . . ".

Dialog, No. 6160495, 1698-1702, Embase No. 86155555, Chapekar et al., "Potentiation of the Cytocial Effect of Human Immune Interferon . . . ".

Dialog, No. 6109766, pp. 359-365, Embse No. 86104826, Hubbell et al., "Synergistic Antiproliferative Effect of Human Interferons in Combination . . . ".

Primary Examiner—John W. Rollins
Attorney, Agent, or Firm—Nixon & Vanderhye

[57] ABSTRACT

Studies of Synergistic combinations of dsRNAs and anti-viral agents in the treatment of viral diseases indicates dsRNA, especially mismatched dsRNA, plays a powerful and versatile role as a core drug in combination therapy for human viral pathogens, notably for ARC and AIDS.

8 Claims, No Drawings

DSRNAS FOR COMBINATION THERAPY IN THE TREATMENT OF VIRAL DISEASES

CROSS-REFERENCES TO RELATED APPLICATIONS

This application is a continuation-in-part of earlier application Ser. No. 028,823 filed Mar. 23, 1987, now abandoned.

BACKGROUND OF THE INVENTION

This invention relates to the use of dsRNA in synergistic combination with other materials that inhibit viral activity or expression to control or in the treatment of viral diseases.

Double-stranded RNAs (dsRNAs), such as poly I.-poly C, can act as biological response modifiers eliciting antiviral, antineoplastic and immunomodulatory activities. Among the pleiotropic effects responsible for these biological responses are induction of interferon (IFN) and other cytokines as well as activation of certain INF-induced enzymes including 2,5-oligoadenylate synthetase and a ribosome-associated protein kinase. These properties make dsRNAs attractive candidates for the treatment of infection by human immunodeficiency virus (HIV), the retrovirus responsible for acquired immunodeficiency syndrome (AIDS). In fact, mismatched dsRNA of the form $r(I)_n \cdot r(C_{12-14}-U)_n$ (Ampligen) has a low toxicity profile in humans, is active against HIV infection both in vitro and in vivo, and is currently in large-scale, controlled clinical trials of AIDS-related complex (ARC).

The American Foundation for AIDS Research (AmFAR) currently lists over 60 drugs being tested for use in treating ARC and AIDS. This enormous potential of single-agent therapy is compounded by possible synergism in combination therapy. Alternatively, combined therapy has the potential for antagonism as demonstrated in vitro with azidothymidine (AZT) and ribavirin. For these reasons, I decided to characterize the full potential of mismatched dsRNA in the treatment of ARC and AIDS. I accomplished this by performing in vitro multiple drug analyses using mismatched dsRNA as a core drug in combination with other agents that together encompassed at least five different modes of attack on this virus. These agents included rIFN-alpha A, rIFN-beta Ser 17 and rIFN-$\gamma$ as cytokines; azidothymidine and phosphonoformate (foscarnet) as inhibitors of reverse trasncription; ribavarin as a putative disrupter of mechanisms governing proper mRNA capping; amphotericin B as a lipid-binding molecule with anti-HIV activity; and castanospermine as an inhibitor of glycoprotein processing (1). One of the drugs, azidothymidine, appeared to act synergistically in vitro with mismatched dsRNA as described in earlier application Ser. No. 028,823 filed Mar. 23, 1987, now abandoned.

In this application, I demonstrate that each drug separately had dose-dependent anti-HIV activity which was synergistic with mismatched dsRNA at the most effective doses.

DESCRIPTION OF THE INVENTION

This invention includes the use of synergistic combinations of dsRNAs, notably mismatched dsRNAs, together with a member of a wide range of antiviral compounds in the treatment of viral diseases. The combination is administered to a patient in an amount sufficient to inhibit viral activity, inhibit viral expression, or both. Pharmaceutical compositions containing a dsRNA and another antivirally-active compound are described and the results of this combination demonstrating synergism reported below.

As an expansion of application Ser. No. 028,823, additional data are here presented verifying the role of dsRNA as a synergistic agent with various other modalities in control of viral expression in general and retroviruses in particular utilizing HIV (AIDS virus) as a prototypic human virus associated with chronic debilitating human disease. Synergism in inhibiting viral activity/expression in unexpectedly seen with a broad range of disparate compounds including cytokines, reverse transcriptase inhibitors, lysophiles and glycoprotein processing inhibitors.

The effective treatment of AIDS has obviously become a growing concern among physicians in nearly all countries around the globe. Azidothymidine, the first drug approved in the United States for the treatment of ARC and AIDS, is extremely toxic. This in vivo toxicity is manifested by approximately 30% of patients receiving azidothymidine requiring blood transfusions. The results of my present experiments suggest that drugs like azidothymidine with high in vivo toxicity can be given at substantially lower, less toxic doses if combined with mismatched dsRNA. Combination therapy may not only reduce the effective dose of a drug required for antiviral activity, thereby reducing its toxicity, but may also improve the absolute antiviral effect as a result of attacking the virus through multiple mechanisms. The pleiotropic activities of mismatched dsRNA together with the synergies reported here suggest that dsRNA in general, and mismatched dsRNA in particular, will be an effective core drug for combination therapy yielding the most effective and least toxic treatment for ARC and AIDS.

Studies with eight different antiviral drugs, representing five different general classes of antivirals, in combination with dsRNA, especially the mismatched dsRNAs as defined in more detail below, demonstrate that dsRNAs, notably mismatched dsRNAs, provide a synergistic complement to antiviral therapy in general, and in the treatment of aids-related complex and AIDS itself specifically. These dsRNAs, when administered in combination with other antiviral drugs known to cause significant toxicity when administered alone and in quantities effective to address the viral condition, have the additional benefit of permitting the clinician to reduce the amount of the toxic member of the combination without adverse affect on the desired therapeutic results of the treatment.

Multiple drug effect analyses with mismatched double-stranded RNA (Ampligen ®, a registered trademark of HEM Research, Inc. of Rockville, Maryland, USA) as a core drug were performed to identify other agents and mechanisms through which mismatched dsRNA may potentiate effective therapeutic intervention in human immunodeficiency virus (HIV) infection. Antiviral activities were defined by a microtiter infection assay utilizing MT-2 cells as targets and HTLV-III$_B$ produced in H9 cells as a virus source. The scope of agents tested included rIFN-alpha A, rIFN-beta SER 17, and rIFN-$\gamma$ as cytokines; azidothymidine and phosphonoformate (Foscarnet) as inhibitores of reverse transcription; ribavirin as a putative inhibitor of proper HIV mRNA capping; amphotericin B as a lipophile; and castanospermine as a glycoprotein processing (glucosidase I) inhibitor. Separately, each drug demonstrated dose-dependent anti-HIV activity and, when used in combination with mismatched dsRNA, demonstrated synergism. Although mismatched dsRNA was synergistic with all three IFNs for anti-HIV activity in microtiter infection assays, it did not potentiate IFN-induced inhibition of virus production in cultures of H9/HTLV-III$_B$ cells. The results of these studies suggest that the pleiotropic activities of dsRNAs differ from those of IFN and may provide synergism in combination therapy with a wide range of antiviral drugs for the treatment of acquired immunodeficiency syndrome (AIDS). The procedures and therapeutic compositions of this invention are intended to include the above-listed agents, as exemplary and illustrative of various classes there named. Various other agents yet to be discovered but synergistic when combination with dsRNAs are also included within the scope of this invention.

By "mismatched dsRNAs" are meant those in which hydrogen bonding (base stacking) between the counterpart strands is relatively intact, i.e., is interrupted on average less than one base pair in every 29 consecutive base residues. The term "mismatched dsRNA" should be understood accordingly.

The dsRNA may be a complex of polyinosinate and a polycytidylate containing a proportion of uracil bases or guanidine bases, e.g., from 1 in 5 to 1 in 30 such bases (poly I. poly $(C_{4-29} \times > U$ or G).

The dsRNA may be of the general formula $rI_n.(C_{12}U)_n$. Other suitable examples of dsRNA are discusses below.

The mismatched dsRNAs preferred for use in the present invention are based on copolynucleotides selected from poly $(C_n,G)$ in which n is an integer having a value of from 4 to 29, and are mismatched analogs of complexes of polyriboinosinic and polyribocytydilic acids, formed by modifying $rI_n.rC_n$ to incorporate unpaired bases (uracil or guanidine) along the polyribocytidylate $(rC_n)$ strand. Alternatively, the dsRNA may be derived from poly (I). poly (C) dsRNA by modifying the ribosyl backbone of polyriboinosinic acid $(rI_n)$ e.g., by including 2'-0-methyl ribosyl residues. These mismatched analogs of $rI_n.rC_n$, preferred ones of which are of the general formula $rI_n.r(C_{11-14},U)_n$ and $rI_n.r(C_{29},G)_n$, are described by Carter and Ts'o in U.S. Pat. Nos. 4,130,641 and 4,024,222 the disclosures of which are hereby incorporated by reference. The dsRNAs described therein generally are suitable for use according to the present invention.

Other examples of mismatched dsRNA for use in the invention include:
poly (I). poly $(C_4,U)$
poly (I). poly $(C_7,U)$
poly (I). poly $(C_{13},U)$
poly (I). poly $(C_{22},U)$
poly (I). poly $(C_{20},G)$
poly (I). poly $(C_{29},G)$ and
poly (I). poly $(C_p)$ 23 G>p When interferon (alpha) is used as the lymphokine, an amount of from 0.01 to 100,000 IRU per milliliter of the patient's body fluid is provided.

The usual amounts of dsRNA administered provide a level of from 0.1 to 1,000 micrograms dsRNA per milliliter of the patient's body fluid. The term body fluid is intended to refer to that solution of serum, salts, vitamins, etc., which circulates within the organism and bathes the tissues. When both agents (a dsRNA and another antiviral compound) are administered they may be administered as a mixture, administered separately but simultaneously, or sequentially. The complementary antiviral used with the dsRNA is administered in quantities consistent with the product labeling or other directions for use and often in somewhat smaller amounts due to the concurrent use of the dsRNA and the synergistic result of the combination.

Administration of a dsRNA and another antiviral agent "in combination" includes presentations in which both agents are administered together as a therapeutic mixture, and also procedures in which the two agents are administered separately but simultaneously, e.g., as through separate intravenous lines into the same individual. Administration "in combination" further includes the separate administration of one of the drugs in which one of the drugs is given first followed shortly by the second.

A group of in vitro studies were undertaken to evaluate Ampligen, a mismatched dsRNA, for combination therapy in the treatment of viral diseases utilizing AIDS virus as a prototypic chronic/subacute human viral pathogen. The materials and methods used are described below.

Cells and Virus - A clone of the HTLV-I-transformed T-cell line MT-2, which exhibits complete cytolysis upon infection with HIV(19), was used as the target for infections in microtiter assays. Virus was prepared from H9/HTLV-III$_B$ culture fluids by low speed centrifugation and 0.45 $\mu$M filtration to remove all cells. Viral titers were determined from 50% tissue culture infectious dose (TCID-50) values obtained by endpoint microtitration on MT-2 cells. All cultures were grown and maintained in RPMI-1640 containing 16% heat-inactivated fetal calf serum and 50 $\mu$g gentamicin (Sigma)/ml.

Antivirals—Human rIFN-$\alpha$A ($>10^8$ IU/mg), rIFN-$\gamma$ ($1.4 \times 10^8$ IU/mg) and azidothymidine were obtained from Hoffman-La-Roche. Human rIFN-$\beta$.Ser 17 ($1.0 \times 10^8$ IU/mg) was obtained from Triton Biosciences. IFNs were calibrated in WISH cells challenged with vesicular stomatitis virus and assayed for cytopathic effect as previously described (2). Reference standards were obtained from the World Health Organization (human IFN-$\alpha$, WHO standard B,69/19 and human IFN-$\beta$, WHO no. G-023-902-527) or the National Institute of Allergy and Infectious Disease (human-IFN-$\gamma$, National Institutes of Health no. Gg23-901-530). Amphotericin B (Fungizone) was obtained from GIBCO, castanospermine from Boehringer Mannheim, ribavirin (Virazole) from Viratel. Inc., and phosphonoformate (Foscarnet) from Astra Alab AB. Mismatched dsRNA (Ampligen) was provided as a lyophilized powder in a salt buffer by HEM Research, Inc., Rockville, Maryland.

Microtiter Infection Assay—Anti-HIV activities were measured in a microtiter infection assay as described (2). Briefly, two-fold, serial dilutions of each drug alone and in fixed-ratio combination with mismatched dsRNA were assayed in triplicate in 96-well microtiter plates. Cytolysis was measured via vital dye (neutral red) uptake by poly-L-lysine adherent cells as an endpoint for infection. Cells were incubated in the presence of drug dilutions for 1 hour prior to addition of virus. In the case of amphotericin B, both virus and cells were preincubated with drug prior to challenge. Cells were infected at a multiplicity of 0.1 so that endpoint cytolysis would be predominantly due to progeny virions synthesized in the presence of the drug. Percent protection was derived from $A_{540}$ values of the dye in test wells relative to the difference in absorption between the cell control and virus control wells using the formula:

$$\% \text{ Protection} = \frac{\text{(test minus virus)}}{\text{(cells minus virus)}}$$

Calculation of Synergy—Combined drug effects were calculated by the multiple drug analysis method of Chou and Talalay using the equation:

$$CI = \frac{(D)_1}{(Dx)_1} + \frac{(D)_2}{(Dx)_2} + \frac{\alpha(D)_1(D)_2}{(Dx)_1(Dx)_2}$$

where Cl is the combination index, $(Dx)_1$ is the dose of drug 1 required to produce x percent effect alone, and $(D)_1$ is the dose of drug 1 required to produce the same x percent effect in combination with $(D)_2$. The values of $(Dx)_2$ and $(D)_2$ are similarly derived from drug 2. The value of $\alpha$ is determined from the plot of the dose effect curve using the median effect equation:

$$fa/fu = (D/Dm)^m$$

where fa is the fraction affected by dose D, fu is the unaffected fraction, Dm is the dose required for 50% effect and m is the slope of the dose-effect curve. For mutually exclusive drugs (i.e., similar mode of action), both drugs alone and their mixture give parallel lines in the median effect plot. Mutually nonexclusive drugs (i.e., independent mode of action) will give parallel lines in the median effect plot but in mixture will give a concave upward curve. If the agents are mutually exclusive, $\alpha$ is 0, and if they are mutually nonexclusive, $\alpha$ is 1. Values obtained assuming mutual nonexclusiveness will always be slightly greater than mutually exclusive drugs. Cl values of $<1$ indicate synergy, values $>1$ indicate antagonism and values equal to 1 indicate additive effects. Our data was analyzed with the assistance of an IBM-PC-compatible computer program.

Reverse Transcriptase Assay—Reverse transcriptase activities in culture fluids were assayed in polyethylene glycol precipitates as described (3) using poly (A).(dT)$_{15}$ as template primer (Boehringer Mannheim) and 25 $\mu$Ci [methyl-$^3$H] dTTP (80.I Ci/mmol, New England Nuclear) per reaction. Review and analysis of these studies has given the following results and conclusions:

Antiviral Activities—The ability of each drug alone and in combination with mismatched dsRNA to protect target cells from HIV infection is shown in Table 1. With the exception of ribavirin, full protection was observed at all concentrations of each drug early in the incubation period immediately following cytolysis in the virus control (no effectors) wells. Virus-induced cytolysis at the lower doses of these drugs occurred one day later and assays were processed again at this time so that dose-dependent relationships could be achieved. Assays were also processed for ribavirin at this time, although full protection was never achieved at any sub-toxic concentration of this drug, even early in the infection process. The most effective ($>10\%$ protection) concentrations of each drug produced greater anti-HIV activity in combination with mismatched dsRNA than when used alone. All drugs were non-toxic to MT-2 cells at the concentrations utilized in these studies.

Multiple Drug Effects—Cl values for mismatched dsRNA in dual combination with eight other anti-HIV drugs at 50% and 95% protections values are given in Table 2. Various degrees of synergism were observed. The greatest degree of synergism was between mismatched dsRNA and rIFN-$\alpha$ where Cl values were the lowest (0.01 to $<0.01$). The least amount of synergism was observed with amphotericin B where Cl values were the highest observed and indicated more of an additive effect at 50% protection Cl=0.90 pr 1/08). Other drugs demonstrating synergism with mismatched dsRNA (Cl values less than 1) were rIFN-$\beta$, rIFN-$\gamma$, azidothymidine, ribavirin, phosphonoformate, amphotericin B and castanospermine. Very little difference was observed if Cl values were calculated on the assumption of mutual exclusiveness versus mutual nonexclusiveness for each drug tested.

TABLE 2

Cl Values for Combined Drug Effects with Mismatched dsRNA as a Core Drug

| Drug | Cl at Following % Protection Values* | | |
|---|---|---|---|
| | 50 | 90 | 95 |
| rIFN-$\alpha$A | 01 | $<.01$ | $<.01$ |
| | (.01) | ($<.01$) | ($<.01$) |
| rIFN-$\beta$ | .34 | .14 | .10 |
| | (.36) | (.14) | (.10) |
| rIFN-$\gamma$ | .55 | .37 | .33 |
| | (.56) | (.37) | (.33) |
| Azidothymidine | .55 | .40 | .37 |
| | (.56) | (.40) | (.37) |
| Ribavirin | .35 | .19 | .15 |
| | (.35) | (.19) | (.15) |
| Phosphonoformate | .58 | .65 | .70 |
| | (.63) | (.68) | (.72) |
| Amphotericin B | .90 | .67 | .65 |
| | (1.08) | (.71) | (.67) |
| Castanospermine | .55 | .21 | .16 |
| | (.61) | (.23) | (.17) |

*Cl values were calculated from the data in Table 1. Values $>1$ indicate antagonism. $<1$ indicate synergism and equal to one indicate an additive effect. Cl values calculated assuming mutual exclusiveness are given along with values obtained assuming mutual nonexclusiveness in parentheses.

Virus Synthesis—virus production in H9/HTLV-III$_B$ cultures was examined in the presence and absence of IFNs, mismatched dsRNA and the combination of these drugs (Table 3). Mismatched dsRNA alone (50 $\mu$g/ml) had very little effect on the virus production (6% decrease) while rIFN-$\alpha$A, rIFN-$\beta$, and rIFN-$\gamma$ (500 IU/ml) inhibited virus production by 53%, 56%, and 20%, respectively. The presence of mismatched dsRNA resulted in a mild reduction, in the inhibition of virus production induced by the IFNs, where this inhibition was decreased from 53% to 47% for rINF-$\alpha$A, from 56% to 51% rIFN-$\beta$, and from 20% to 15% for rINF-$\gamma$. Other studies (not shown) indicate these concentrations of mismatched dsRNA and rIFNs alone or in combination had no effect on cell division.

TABLE 3

Effect of Mismatched dsRNA on IFN-Induced Inhibition of HIV Production

| Effector* | cpm RT/ml ($\times 10^{-3}$) | Avg. cmp RT/ml ($\times 10^{-3}$) | % Decrease |
|---|---|---|---|
| Control - 1 | 877 | 910 | — |

TABLE 3-continued
Effect of Mismatched dsRNA on IFN-Induced Inhibition of HIV Production

| Effector* | cpm RT/ml ($\times 10^{-3}$) | Avg. cmp RT/ml ($\times 10^{-3}$) | % Decrease |
| --- | --- | --- | --- |
| Control - 2 | 943 | | |
| Mismatched dsRNA - 1 | 896 | 852 | 6 |
| Mismatched dsRNA - 2 | 807 | | |
| rIFN-αA - 1 | 426 | 428 | 53 |
| rIFN-αA - 2 | 430 | | |
| rIFN-β - 1 | 396 | 398 | 56 |
| rIFN-β - 2 | 400 | | |
| Mismatched dsRNA + rIFN-αA - 1 | 418 | 479 | 47 |
| Mismatched dsRNA + rIFN-αA - 2 | 540 | | |
| Mismatched dsRNA + rIFN-β - 1 | 411 | 448 | 51 |
| Mismatched dsRNA + rIFN-β - 2 | 485 | | |
| Control - 3 | 1,945 | 2,013 | — |
| Control - 4 | 2,081 | | |
| rIFN-γ - 1 | 1,508 | 1,602 | 20 |
| rIFN-γ - 2 | 1,696 | | |
| Mismatched dsRNA + rIFN-γ - 1 | 1,669 | 1,704 | 15 |
| Mismatched dsRNA + rIFN-γ - 2 | 1,738 | | |

*Duplicate cultures with equal densities of washed H9/HTLV-III$_B$ cells were incubated in the presence and absence of effectors for 48 hours. Conditioned culture fluids were then harvested and assayed for reverse transcriptase activity. Recombinant IFN-γ ± mismatched dsRNA was tested in a second experiment and therefore had a separate set of controls. Mismatched dsRNA = 50 μg/ml, IFNs = 500 IU/ml.

The synergies observed in this study between mismatched dsRNA and five classes of anti-HIV drugs suggest that mismatched dsRNA may have a powerful and versatile role as a core drug in combination therapy for ARC and AIDS. Double-stranded RNAs, including mismatched dsRNA, activate IFN-induced enzymes involved in the establishment of an antiviral state, including 2,5-oligoadenylate synthetase and a ribosome-associated protein kinase. Recently, I observed that 2,5-oligoadenylates inhibit retroviral reverse transcriptases, a finding which suggests that activation of 2,5-oligoadenylate synthetase by mismatched dsRNA may represent a unique mechanism for antiviral activity against viruses that require reverse transcription for replication. Most importantly, not all of the pleiotropic activities of IFNs appear to be shared with mismatched dsRNA. This is exemplified by the fact that flu-like side effects of IFN therapy are not present during mismatched dsRNA therapy, as well as the finding that mismatched dsRNA neither inhibited HIV production as did IFN, nor potentiated this activity of IFN's (see Table 3). These latter results are in contrast to the synergism observed between mismatched dsRNA and the IFNs on establishing an antiviral state (see Table 2), further suggesting that these drugs have common as well as distinct pathways for antiviral activity.

Another class of anti-HIV drugs, the inhibitors of reverse transcription, I have also found to be synergistic with mismatched dsRNA. The two inhibitors used in this study were azidothymidine and foscarnet. Azidothymidine, a thymidine analog, becomes phophorylated intracellularly and is incorporated into nascent DNA where it causes premature chain termination. Phosphorylated azidothymidine is utilized by reverse transcriptase 100 times more effectively than by cellular DNA polymerases, thus allowing a seemingly large window of selectivity. Phosphonoformate, (Foscarnet) another inhibitor of reverse transcription, has strong anti-HIV activity in vitro in addition to selectively inhibiting influenza virus RNA polymerase and herpes virus DNA polymerase. Both of these drugs demonstrated potent, selective inhibition of HIV in the microtiter infection assay; see Table 1. Their observed synergism with mismatched dsRNA (see Table 2) suggests that such synergism may also be observed with other inhibitors of reverse transcription.

Ribavirin may represent a class of anti-HIV drugs which interfere with 5'-mRNA processing. Although the mechanism of antiviral activity of ribavirin is not clear, this drug is thought to compete with quanosine in the formation of mRNA cap structures and/or interfere with the functional methylation of these molecules. Other inhibitors of functional HIV mRNAs, such as antisense DNAs, should also exhibit synergy of this anti-HIV mechanism with mismatched dsRNA.

Amphotericin B, a polyene macrolide antifungal antibiotic which interacts with sterols and binds to them irreversibly, represents yet another unique class of agents that are active against a variety of lipid-enveloped viruses, including HIV. Although amphotericin B exhibits severe in vivo toxicities, the methyl ester form of this drug also exhibits anti-HIV activity and has a low cellular toxicity profile in vitro. Therefore, amphotericin B methyl ester will be more beneficial in combination therapy with mismatched dsRNA than the parent compound.

The final agent demonstrating synergism with mismatched dsRNA was castanospermine. Castanospermine is a plant alkaloid which inhibits glycoprotein processing, and was investigated because of the envelope of HIV contains two heavily glycosylated proteins, gp120 as an outer membrane glycoprotein and gp41 as a transmembrane glycoprotein. Interaction between gp120 and the OKT4 surface antigen of T cells, which acts as receptor for the virus, is partly responsible for the cellular tropism of HIV. Recent studies by others with glycolases and lectins have shown that protein glycosylation plays an important role in gp120-LKT4 interaction and HIV infection. Maturation of glycoproteins is dependent on a series of enzymes for the processing of carbohydrate moieties which usually results in the transformation of high-mannose to complex-type oligasaccharides. Castanospermine inhibits glucosidase I which results in a high-mannose type N-glycosylated protein. Under conditions of infection by progeny virions synthesized in the presence of castanospermine, the infectivity of HIV was attenuated (see Table 1). This attenuation was independent of any effect that castanospermine may have had on the state of receptor glycosylation and was actually due to a reduction in infectious virus yield, as determined by TCID-50 assays, with no effect on overall virus production as measured by virus-associated reverse transcriptase activity. The finding that this anti-HIV activity is synergistic with mismatched dsRNA (Table 2) suggests that mismatched dsRNA will be synergistic with agents which interfere with HIV receptor binding. These agents will include neutralizing antibodies, blocking peptides such as peptide "T", or other inhibitors of glycoprotein processing.

AMPLIGEN® is a registered trademark of HEM Research, Inc., Rockville, MD, USA.

Table of References

1. Elbein, A. D. (1987) Inhibitors of the Biosynthesis and Processing of N-linked Oligosaccharide Chains. Ann. Rev. Biochem. 56,497-534
2. Montefiori, D. C., Robinson, W. E., Jr., Schuffman, S. S. and Mitchell, W. M. (1987) Evaluation of Antiviral Drugs and Neutralizing Antibodies Against Human Immunodeficiency Virus by a Rapid and Sensitive Microtiter Infection Assay. J. Clin Microbiol. (In press)
3. Poiesz, B. J., Ruscetti, F. W., Gazder, A. F., Bunn, P. A., Minna, J. D. and Gallo, R. C. (1980) Detection and Isolation of Type C Retrovirus Particles From Fresh and Cultured Lymphocytes of a Patient With Cutaneous T-cell Lymphoma. Proc. Natl. Acad. Sci. USA 77, 7415-7419.

What is claimed is:

1. A pharmaceutical composition for the treatment of retroviral infections comprising an effective amount of an inhibitor of reserve transcriptase in combination with the mismatched dsRNA $rI_n \cdot r(C_{11-14},U)_n$ in an amount sufficient to result in a level of 0.1 to 1000 micrograms of the dsRNA per milliliter of the patient's body fluid.

2. The pharmaceutical composition of claim 1, in which the inhibitor of reverse transcriptase is azidothymidine.

3. The pharmaceutical composition of claim 1, in which the inhibitor of reverse transcriptase is phosphonoformate.

4. A method of treating a retroviral disease in a person having same comprising administering to that person, in combination, a therapeutic amount of (1) an antiviral agent selected from the group consisting of rIFN-$\alpha$, rIFN-$\beta$, rIFN-$\gamma$ and a reverse transcriptase inhibitor, and (2) the mismatched dsRNA $rI_n \cdot r(C_{11-14},U)_n$ in an amount sufficient to result in a level of 0.01 to 1000 micrograms per milliliter of the patient's body fluid.

5. The method of claim 4, in which the reverse transcriptase inhibitor is azidothymidine or phosphonoformate.

6. The method of claim 4, in which the dsRNA contains regions of bond breakage and the dsRNA exhibits the favorable therapeutic ratio property of $rI_n \cdot r(C_{11-14},U)_n$.

7. The method of claim 4, in which the virus is HIV.

8. The method of claim 7, in which the person is treated for AIDS-related complex.

* * * * *